United States Patent
Peterson

(10) Patent No.: US 9,149,387 B2
(45) Date of Patent: Oct. 6, 2015

(54) VARYING MATERIAL PROPERTIES OF A SINGLE FLUIDIC LINE IN OPHTHALMOLOGY TUBING

(75) Inventor: Robert H. Peterson, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 1798 days.

(21) Appl. No.: 12/204,284

(22) Filed: Sep. 4, 2008

(65) Prior Publication Data

US 2010/0057092 A1     Mar. 4, 2010

(51) Int. Cl.
  *F16L 11/00*     (2006.01)
  *A61F 9/007*     (2006.01)
  *A61M 39/08*     (2006.01)

(52) U.S. Cl.
  CPC ............ *A61F 9/00736* (2013.01); *A61M 39/08* (2013.01)

(58) Field of Classification Search
  USPC .................................................. 138/116, 119
  See application file for complete search history.

(56) References Cited

U.S. PATENT DOCUMENTS

| | | |
|---|---|---|
| 3,336,764 A | 8/1967 | Chambers |
| 3,589,363 A | 6/1971 | Banko |
| 3,994,297 A | 11/1976 | Kopf |
| 3,997,097 A | 12/1976 | Embury |
| 4,223,676 A | 9/1980 | Wuchinich |
| 4,246,902 A | 1/1981 | Martinez |
| 4,493,694 A | 1/1985 | Wuchinich |
| 4,515,583 A | 5/1985 | Sorich |
| 4,553,957 A | 11/1985 | Williams et al. |
| 4,589,415 A | 5/1986 | Haaga |
| 4,609,368 A | 9/1986 | Dotson, Jr. |
| 4,627,844 A | 12/1986 | Schmitt |
| 4,662,404 A * | 5/1987 | LeVeen et al. ................ 138/120 |
| 4,750,902 A | 6/1988 | Wuchinich et al. |
| 4,816,018 A | 3/1989 | Parisi |
| 4,869,715 A | 9/1989 | Sherburne |
| 4,922,902 A | 5/1990 | Wuchinich |
| 4,954,055 A | 9/1990 | Raible et al. |
| 4,989,583 A | 2/1991 | Hood |
| 5,154,694 A | 10/1992 | Kelman |

(Continued)

FOREIGN PATENT DOCUMENTS

| | | |
|---|---|---|
| DE | 3942192 | 6/1991 |
| DE | 10233053 A1 | 2/2004 |

(Continued)

OTHER PUBLICATIONS

Kishimoto, Makoto, MD, PESAVER—Super Irrigation System, Techniques in Ophthalmology, Mar. 2006, 6 pages, vol. 4, Issue 1, Lippincott Williams & Wilkins, Shiga, Japan.

(Continued)

*Primary Examiner* — James Hook

(57) ABSTRACT

Twin bore ophthalmologic tubing includes first and second tubes. The second tube has portions of differing hardness with one of the portions being at an end of that tube. The second tube has a portion at its other end with about the same hardness. Portions of the first and the second tubes may have about the same hardness. In some embodiments, portions of the first and second tubes with the same hardness can correspond to each other along the tubing. One of the portions can have a hardness of 80 to 90 shore A while the other portion can be 60 to 70 shore A. In some embodiments, portions with 60 to 70 shore A hardness can be about six to twelve inches long.

5 Claims, 3 Drawing Sheets

(56) References Cited

U.S. PATENT DOCUMENTS

| | | | |
|---|---|---|---|
| 5,242,385 A | 9/1993 | Strukel | |
| 5,261,885 A | 11/1993 | Lui | |
| 5,305,799 A | 4/1994 | Dal Palu | |
| 5,318,515 A | 6/1994 | Wilk | |
| 5,340,330 A | 8/1994 | Dolson et al. | |
| 5,358,493 A | 10/1994 | Schweich et al. | |
| 5,359,996 A | 11/1994 | Hood | |
| 5,399,160 A | 3/1995 | Dunberger et al. | |
| 5,476,448 A | 12/1995 | Urich | |
| 5,533,878 A | 7/1996 | Iwata | |
| 5,549,547 A | 8/1996 | Cohen et al. | |
| 5,560,398 A * | 10/1996 | Pfleger | 138/121 |
| 5,568,944 A * | 10/1996 | Kawasaki | 285/21.1 |
| 5,616,120 A | 4/1997 | Andrew et al. | |
| 5,653,265 A * | 8/1997 | Nakagawa et al. | 138/121 |
| 5,662,144 A | 9/1997 | Lo et al. | |
| 5,685,841 A | 11/1997 | Mackool | |
| 5,700,240 A | 12/1997 | Barwick et al. | |
| 5,704,401 A * | 1/1998 | Fukui et al. | 138/121 |
| 5,873,851 A | 2/1999 | Nilsson | |
| 5,897,537 A * | 4/1999 | Berg et al. | 604/525 |
| 5,947,953 A | 9/1999 | Ash et al. | |
| 5,988,700 A | 11/1999 | Prichard | |
| 6,050,971 A | 4/2000 | Garnier et al. | |
| 6,119,731 A * | 9/2000 | Nakagawa et al. | 138/121 |
| 6,159,175 A | 12/2000 | Strukel et al. | |
| 6,283,974 B1 | 9/2001 | Alexander | |
| 6,319,454 B1 | 11/2001 | Nakagawa et al. | |
| 6,579,259 B2 | 6/2003 | Stevens et al. | |
| 6,599,271 B1 | 7/2003 | Easley | |
| 6,629,948 B2 | 10/2003 | Rockley et al. | |
| 6,849,068 B1 | 2/2005 | Bagaoisan et al. | |
| 6,878,142 B2 | 4/2005 | Lawrence et al. | |
| 6,913,041 B2 | 7/2005 | Lehnhardt et al. | |
| 6,960,182 B2 | 11/2005 | Moutafis et al. | |
| 7,172,578 B2 | 2/2007 | Mackool | |
| 7,371,224 B2 | 5/2008 | Haischmann et al. | |
| 7,484,769 B2 | 2/2009 | Domash et al. | |
| 2002/0022810 A1 | 2/2002 | Urich | |
| 2002/0055725 A1 | 5/2002 | Verkaart et al. | |
| 2002/0128560 A1 | 9/2002 | Urich | |
| 2003/0195460 A1 | 10/2003 | Kadziauskas | |
| 2004/0034333 A1* | 2/2004 | Seese et al. | 604/523 |
| 2004/0039351 A1 | 2/2004 | Barrett | |
| 2004/0116901 A1 | 6/2004 | Appling | |
| 2005/0070859 A1 | 3/2005 | Cull et al. | |
| 2005/0080375 A1 | 4/2005 | Kadziauskas et al. | |
| 2005/0096585 A1 | 5/2005 | Schon et al. | |
| 2005/0135974 A1 | 6/2005 | Harvey et al. | |
| 2006/0041220 A1 | 2/2006 | Boukhny et al. | |
| 2006/0084937 A1 | 4/2006 | Akahoshi | |
| 2006/0135974 A1 | 6/2006 | Perkins | |
| 2006/0161101 A1 | 7/2006 | Dimalanta et al. | |
| 2006/0173404 A1 | 8/2006 | Urich | |
| 2006/0224163 A1 | 10/2006 | Sutton | |
| 2006/0253062 A1 | 11/2006 | Liao et al. | |
| 2006/0293646 A1 | 12/2006 | Whayne et al. | |
| 2007/0032777 A1 | 2/2007 | Perkins et al. | |
| 2007/0043338 A1 | 2/2007 | Moll et al. | |
| 2007/0043351 A1 | 2/2007 | Fleischman et al. | |
| 2007/0070859 A1 | 3/2007 | Hirayama | |
| 2007/0078440 A1 | 4/2007 | Perkins et al. | |
| 2007/0098578 A1 | 5/2007 | Morgan | |
| 2007/0100285 A1 | 5/2007 | Griffin et al. | |
| 2007/0149919 A1 | 6/2007 | Perkins et al. | |
| 2007/0149950 A1 | 6/2007 | Perkins et al. | |
| 2007/0250040 A1* | 10/2007 | Provost et al. | 604/525 |
| 2007/0267012 A1* | 11/2007 | McCarthy | 128/201.11 |
| 2008/0125699 A1 | 5/2008 | Davis et al. | |
| 2008/0300539 A1* | 12/2008 | Vreeman et al. | 604/103.06 |
| 2010/0056991 A1 | 3/2010 | Dimalanta, Jr. et al. | |

FOREIGN PATENT DOCUMENTS

| | | |
|---|---|---|
| DE | 10233053 B4 | 2/2005 |
| EP | 1716828 A1 | 11/2006 |
| EP | 1716828 B1 | 5/2008 |
| EP | 1917987 A2 | 5/2008 |
| EP | 1917987 A3 | 8/2008 |
| EP | 1917987 B1 | 12/2009 |
| EP | 2161046 A1 | 3/2010 |
| FR | 964069 | 8/1950 |
| JP | H05-31158 | 2/1993 |
| JP | 05305096 A | 11/1993 |
| JP | 10071166 A | 3/1998 |
| JP | 2008-114070 A | 5/2008 |
| TW | 333460 | 6/1998 |
| WO | 88/03421 A1 | 5/1988 |
| WO | WO 98/07398 A1 | 2/1998 |
| WO | WO 99/38549 A1 | 8/1999 |
| WO | WO 01/74427 A1 | 10/2001 |
| WO | WO 2006/069016 A1 | 6/2006 |
| WO | 2010/027924 A2 | 3/2010 |
| WO | WO 2010/027619 A2 | 3/2010 |
| WO | 2010/027924 A3 | 4/2010 |
| WO | WO 2010/027619 A3 | 4/2010 |

OTHER PUBLICATIONS

Prosecution History of U.S. Appl. No. 11/591,980, filed Nov. 2, 2006, 471 pages.
International Searching Authority, Written Opinion of the International Searching Authority, PCT/US09/053708, Mar. 15, 2010, 6 pages.
Prosecution History of EP Patent Application No. 09791487.3, Grant No. EP2344096, granted Nov. 12, 2012, 246 pgs.
Hook, James F., Non-Final Office Action, U.S. Appl. No. 12/540,014, Feb. 16, 2012, 24 pages.
Dr. Ulrich Naumann, Notice of Opposition and EPO Communication, Sep. 23, 2010, 25 pages.
Wolgang Ruchert, Contribution to the Development of an Elastic Lens with a Variable Focal Length for Use in an Artificial Accommodation System (D8 document referenced in the Notice of Opposition dated Sep. 23, 2010 above).
Notice of Allowance of U.S. Appl. No. 11/591,980, filed Nov. 2, 2006, dated Mar. 14, 2011, 14 pages.
European Patent Office, European Search Report, European Patent Application No. EP 09 17 5773.2, Jan. 28, 2010, 5 pages.
International Searching Authority, Written Opinion of the International Searching Authority, PCT/US09/055415, Mar. 5, 2010, 6 pages.
International Searching Authority, International Search Report, PCT/US09/055415, Mar. 5, 2010, 3 pages.
Hook, James F., Final Office Action, U.S. Appl. No. 12/540,014, Jul. 23, 2012, 2012, 7 pages.

\* cited by examiner

VARYING MATERIAL PROPERTIES OF A SINGLE FLUIDIC LINE IN OPHTHALMOLOGY TUBING

BACKGROUND OF THE INVENTION

This invention relates generally to the field of ophthalmologic surgery and more particularly to an apparatus and methods for removing cataracts.

The human eye functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light that can be transmitted to the retina. This deficiency is medically known as a cataract. An accepted treatment for cataracts is to surgically remove the cataract and replace the lens with an artificial intraocular lens (IOL). In the United States, the majority of cataractous lenses are removed using a surgical technique called phacoemulsification. During this procedure, a thin needle with a distal cutting tip is inserted into the diseased lens and vibrated ultrasonically. The vibrating cutting tip liquefies or emulsifies the lens so that the lens may be aspirated from the eye. The diseased lens, once removed, is replaced by an artificial intraocular lens (IOL).

A typical ultrasonic surgical device suitable for an ophthalmic procedure includes an ultrasonically driven hand piece, an attached cutting tip, an irrigating sleeve and an electronic control console. A liquefaction hand piece may also be used. The hand piece assembly is attached to the control console by an electric cable or connector and flexible tubing. A surgeon controls the amount of ultrasound power that is delivered to the cutting tip of the hand piece and applied to tissue at any given time by depressing a foot pedal. Flexible tubing supplies irrigation fluid to and draws aspiration fluid from the eye through the hand piece assembly. Typically, this flexible tubing has a single degree of pliability or hardness. The inventors have discovered that varying this degree of pliability or hardness provides benefits over traditional tubing.

SUMMARY OF THE INVENTION

Embodiments of the present disclosure provide twin bore ophthalmologic tubing that eliminates, or at least substantially reduces, the shortcomings of previously available twin bore ophthalmologic tubing.

One embodiment provides twin bore ophthalmologic tubing for use with a fluidics cassette and a handpiece of an ophthalmologic system. The ophthalmologic system can be a phacoemulsification, liquefaction, or other type of surgical system utilizing irrigation/aspiration handpieces. The twin bore ophthalmologic tubing can include a first sterilized tube and a second sterilized tube joined along substantially the length of the twin bore ophthalmologic tubing. The tubes can have ends adapted for connection to the fluidics cassette and to the handpiece. The second sterilized tube can have two portions of differing hardness with one of the portions being at one of the ends of the second sterilized tube. The first portion can be about 6" to about 12" long and can have a hardness of about 60 shore A to about 70 shore A while the other portion can have a hardness of about 80 shore A to about 90 shore A. In various embodiments, the second sterilized tube can have another portion at the other end of the second sterilized tube with about the same hardness as the first end portion. In some embodiments, the first sterilized tube can have portions of differing hardness. Portions of the first and the second sterilized tubes can have about the same hardness which corresponds to each other along a portion of the twin bore ophthalmologic tubing.

Embodiments provide twin bore ophthalmologic tubing with low compliance and low resistance to movement of the twin bore ophthalmologic tubing (even when connected to surgical handpieces and fluidics cassettes). Embodiments provide twin bore ophthalmologic tubing with rapid vacuum rise times and good occlusion break response in the aspiration line of the twin bore ophthalmologic tubing. Twin bore ophthalmologic tubing of embodiments are provided which allow characteristics such as compliance, navigability, occlusion break response, and vacuum rise time to be controlled by selecting hardness levels for various portions of the twin bore ophthalmologic tubing.

These, and other, aspects will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the disclosure, and the disclosure includes all such substitutions, modifications, additions, or rearrangements.

BRIEF DESCRIPTION OF THE FIGURES

A more complete understanding of the disclosure and the advantages thereof may be acquired by referring to the following description, taken in conjunction with the accompanying drawings in which like reference numbers generally indicate like features and wherein.

DETAILED DESCRIPTION

Various embodiments of the disclosure are illustrated in the FIGURES, like numerals being generally used to refer to like and corresponding parts of the various drawings. Embodiments of the disclosure provide apparatus and methods for cataract extraction.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example", "for instance", "e.g.", "in one embodiment".

Figure 1:
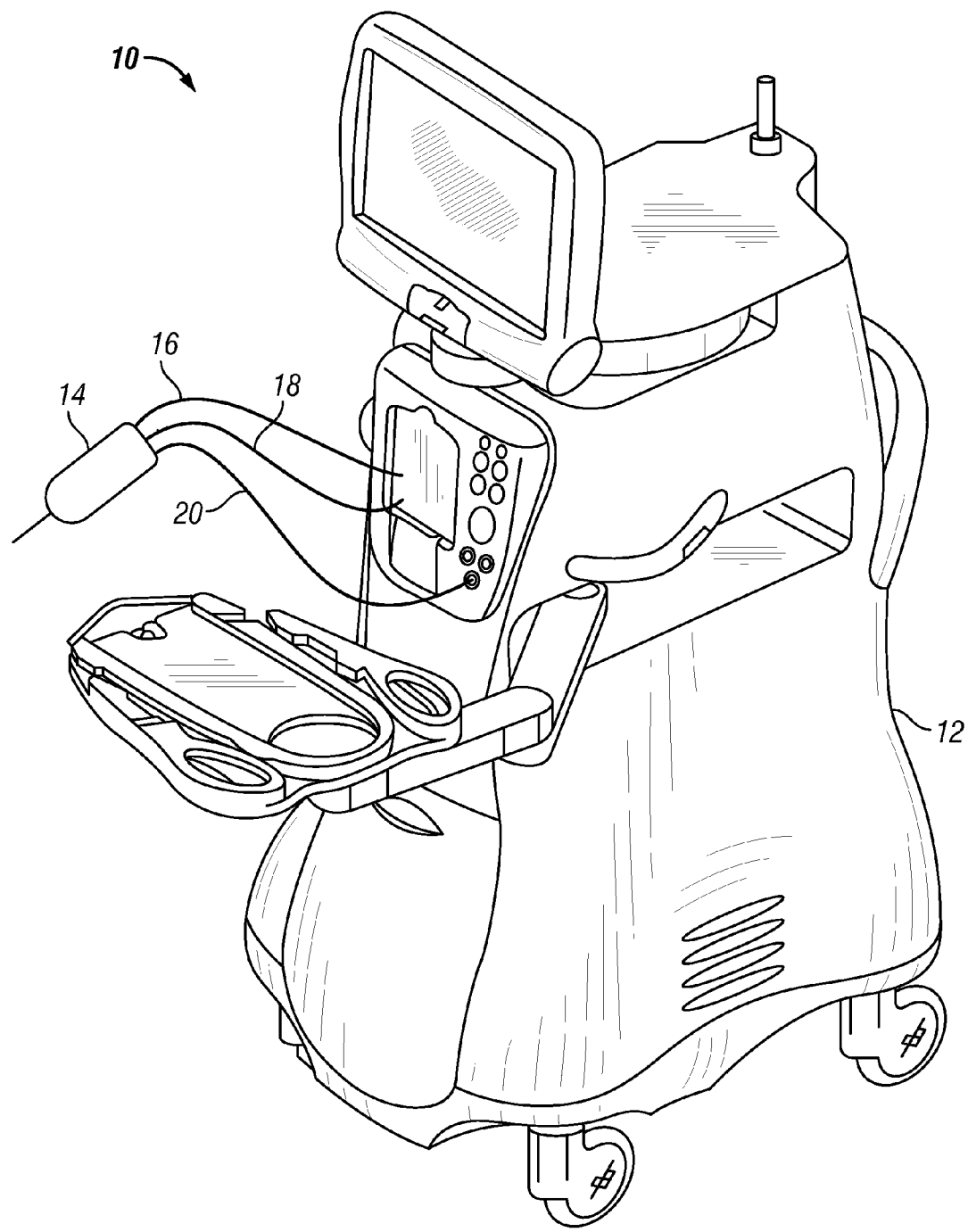
FIG. 1 illustrates a perspective view of one embodiment of a surgical system.

As illustrated in FIG. 1, system 10 can include one embodiment of control console 12 and handpiece 14. System 10 may be any suitable system, such as the INFINITI®. Vision System available from Alcon Laboratories, Inc., Fort Worth, Tex. Handpiece 14 may be any suitable handpiece, such as the AQUALASE® handpiece available from Alcon Laboratories, Inc., Fort Worth, Tex. System 10 can be connected to control console 12 by fluid tubes 16 and 18, and electrically connected to control console 12 by electrical cable 20. Control console 12 can contain appropriate hardware and software (not shown, but well-known in the art) for providing control signals to handpiece 14.

Figure 2:
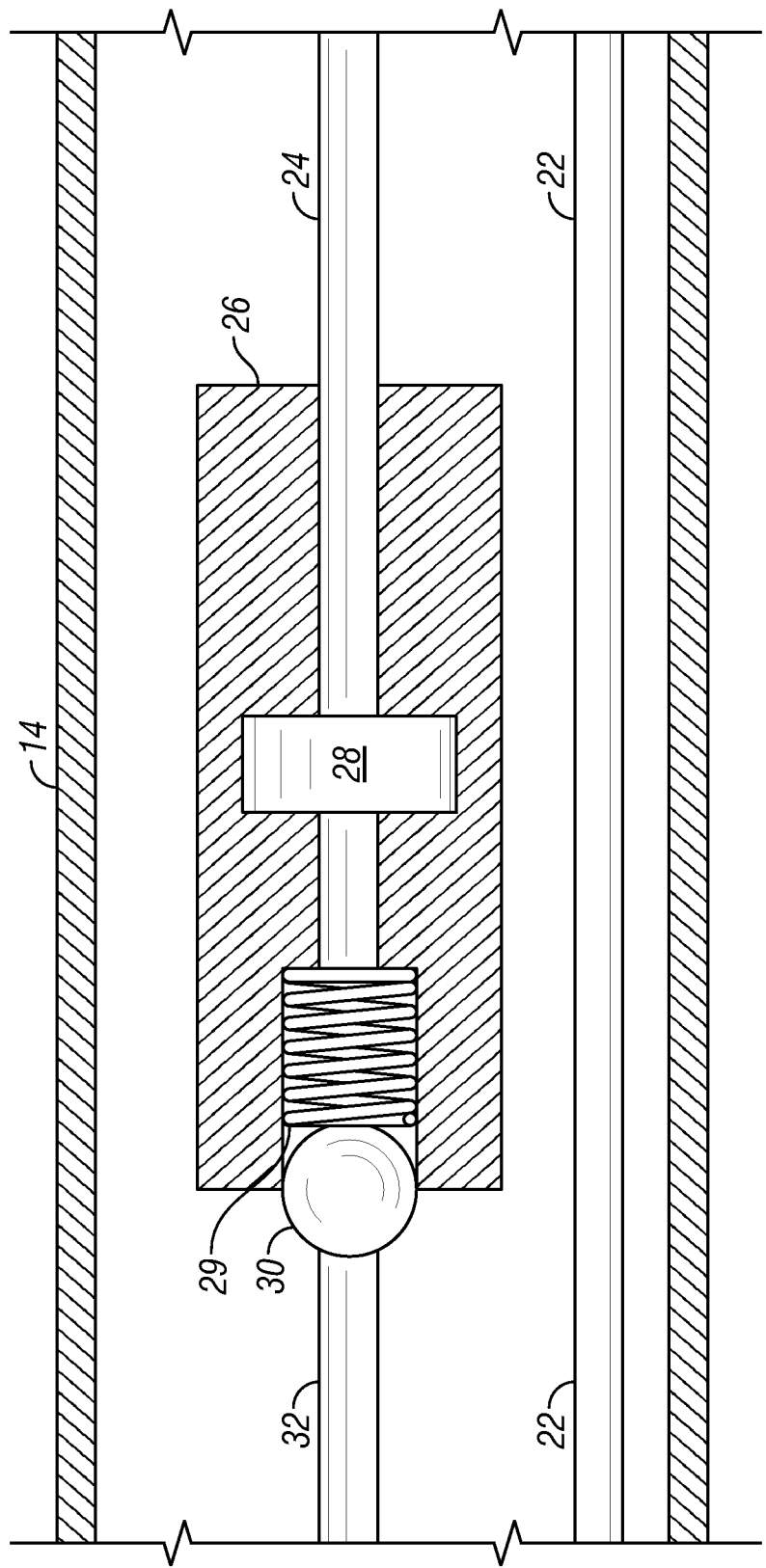
FIG. 2 illustrates a cross sectional view of one embodiment of a liquefaction handpiece.

As illustrated in FIG. 2, embodiments of handpieces 14 for practicing liquefaction techniques generally includes aspiration line 22 (connected to control console 12 through tube 18) and irrigation line 24 (connected to control console 12 by tube 16). Irrigation line 24 provides sterile irrigation fluid to pulse engine 26. Pulse engine 26 contains boiling chamber 28 that produces pressurized pulses of irrigation fluid. Irrigation fluid boiled in boiling chamber 28 exits pulse engine 26 through irrigation line 24. The pressure of the pulse exiting pulse engine 26 through irrigation line 24 is determined by the size and duration of the electrical drive signal sent to pulse engine 26 through cable 20 by control console 12.

As illustrated in FIG. 2, one embodiment of handpiece 14 includes spring 29 which biases check valve 30 closed. In some embodiments, check valve 30 opens when some positive differential pressure (a "cracking pressure") is applied across it. In some situations, sufficient cracking pressure to open check valve 30 can be supplied by one bag of irrigation fluid (for instance balanced saline solution (BSS)) hanging above, and in communication with, handpiece 14. In some situations a second bag (or more) of irrigation fluid can be hung above, and in communication with, the first bag of irrigation fluid to supply sufficient pressure to open check valve 30.

Figure 3:
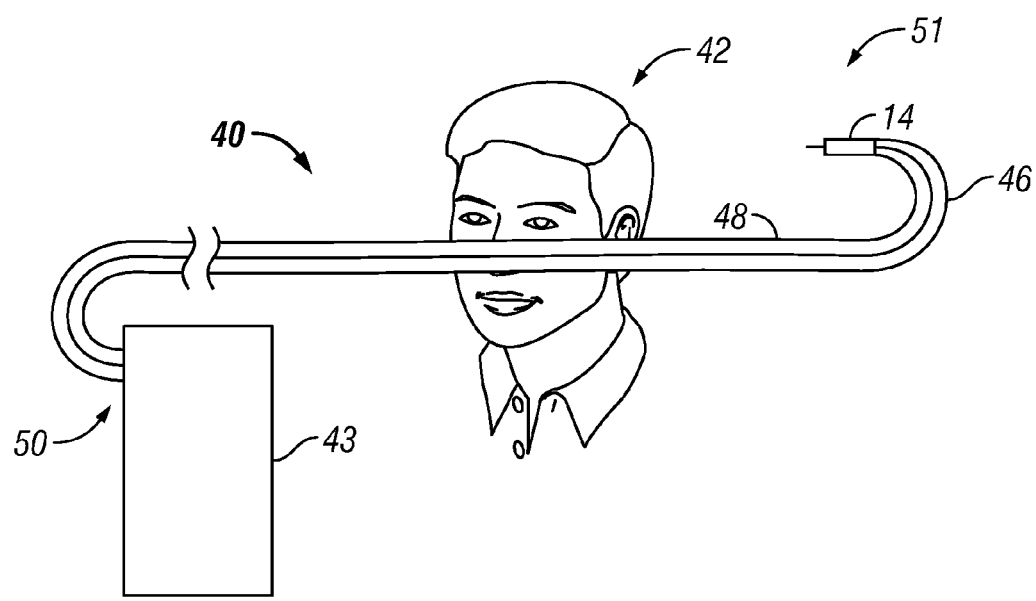
FIG. 3 illustrates a top plan view of one embodiment of a surgical system.
Figure 4:
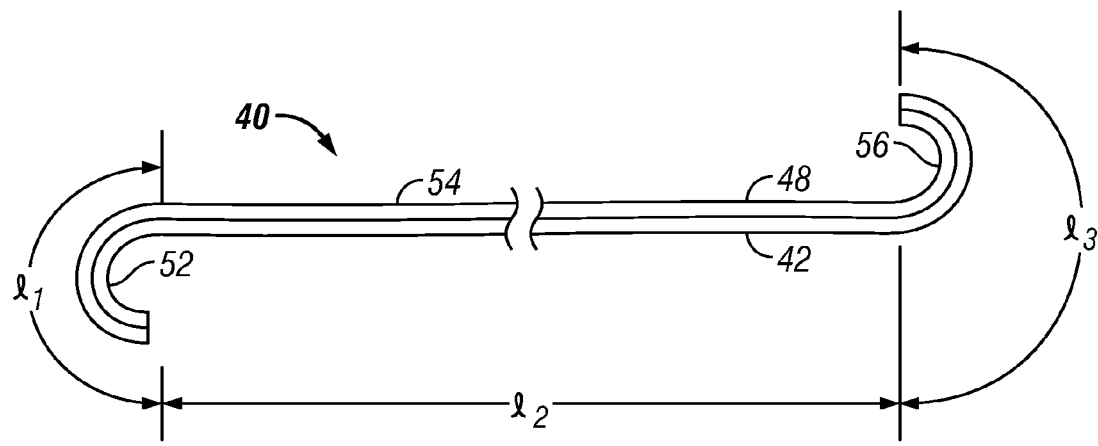
FIG. 4 illustrates a top plan view of one embodiment of a surgical system.

With reference now to FIG. 3, one embodiment of twin bore ophthalmologic tubing 40 is illustrated. Patient 42 is also illustrated. Twin bore ophthalmologic tubing 40 can be used with phacoemulsification, liquefaction, or other surgical systems which utilize irrigation/aspiration handpieces. Twin bore ophthalmologic tubing 40 includes irrigation tube 46, aspiration tube 48, proximal end 50, distal end 51, proximal end portion 52, mid portion 54, and distal end portion 56. Irrigation tube 46 and aspiration tube 48 may be joined to each other (or formed together via extrusion, injection molding, etc.) along substantially the length of twin bore ophthalmologic tubing 40. At proximal and distal ends 50 and 51, irrigation tube 46 and aspiration tube 48 can separate from each other to facilitate connecting twin bore ophthalmologic tubing 40 to certain handpieces 14 and fluidics modules (including the fluidics cassette) 43, control consoles, or the like for receiving and discharging liquid. Proximal and distal ends 50 and 51 can include adapters for connecting twin bore ophthalmologic tubing 40 to fluidics cassette(s) (which can be placed in fluidics modules 43), handpieces 14, etc. as desired or proximal and distal ends 50 and 51 can be dimensioned and shape to slidably engage, and seal against, ports on such devices. Proximal end portion 52 may have length 11, mid portion 54 can have length 12, and distal end portion 56 can have length 13. Lengths 11 and 13 can be about 6" to 12" in some embodiments and, more particularly, about 12" in some embodiments.

As surgical personnel operate on patient 42 using handpiece 14 to perform certain delicate techniques (e.g., phacoemulsification, liquefaction or other methods of extraction of cataracts), irrigation fluid can flow from fluidics module 43 through irrigation tube 46 and into handpiece 14. Within handpiece 14, the liquefaction pulse engine 26 can generate pulses of warmed irrigation fluid which surgical personnel can direct at targeted tissues using handpiece 14. Vacuum applied to proximal end 50 of aspiration line 48 can cause aspiration of the irrigation fluid (and tissues removed therewith) from patient 42 via aspiration line 48. The irrigation fluid, under the influence of the vacuum, can flow from handpiece 14, through aspiration line 48, and into fluidics module 43. As the fluidics module 43 aspirates out the tissue from the patient 42, through the handpiece, pressure variations can develop as a results of occlusion or partial occlusion of the distal end of the handpiece. It is typically desired to avoid these pressure variations.

In some embodiments, aspiration tube 48 can comply with variations in the pressure therein as surgical personnel utilize handpiece 14 to extract and aspirate tissues from patient 42. In some embodiments, aspiration tube 48 can be of sufficient hardness to prevent, or limit, compliance of aspiration tube 48 with the vacuum pressure which might be therein. Thus, at least some aspects of ophthalmologic surgery call for aspiration tubes 48 made from materials having relatively high hardness. Aspiration tubes 48 having relatively high hardness are provided by some embodiments which exhibit little or no compliance. Aspiration tubes 48 can therefore store little or no energy during occlusions. Irrigation tubes 46 can also exhibit little or no compliance in some embodiments although compliance of irrigation tubes 46 may not be a factor in some situations.

As surgical personnel operate to extract cataracts, perform cortical cleanup, etc. on patient 42, surgical personnel may desire to position themselves about patient 42 to observe patient 42, observe various anatomical features of patient 42, navigate handpiece 14, perform surgical techniques using handpiece 14, etc. In some situations, it can happen that surgical personnel may wish to navigate handpiece 14 into certain position(s) at which they desire twin bore ophthalmologic tubing 40 to bend through some arc. For instance, surgical personnel may desire to bring twin bore ophthalmologic tubing 40 across patient 42, turn distal end 51 though some arc (such as 180 degrees), and approach patient 42 with handpiece 14 from the side of patient 42 which is opposite fluidics module 43. In certain situations, surgical personnel may desire to bend proximal end 50 through some arc adjacent to fluidics module 43. Thus, in certain situations, surgical personnel may desire that twin bore ophthalmologic tubing 40 follow a relatively convoluted path as illustrated by FIG. 3.

Hardness levels (and thereby stiffness) of irrigation tube 46 and aspiration tube 48 can create reaction forces, moments, torques, etc. in irrigation tube 46 and aspiration tube 48, respectively. Such reactions can interfere with potentially delicate techniques which surgical personnel may be performing with handpiece 14. Surgery can therefore be complicated by hardness of irrigation tube 46, aspiration tube 48, or both. Thus, at least one aspect of ophthalmologic surgery (for instance, navigability of handpiece 14) can call for irrigation tubes 46 and aspiration tubes 48 made from materials having relatively low hardness and thereby more flexible. Other aspects of ophthalmologic surgery besides navigability (for instance, compliance of irrigation tube 46 and aspiration tube 48) can call for irrigation tubes 46 and aspiration tubes 48 made from materials having relatively high hardness. Thus, compliance can call for tubes of relatively high hardness while navigability can call for tubes of relatively low hardness.

In some embodiments, end portions 52 and 56 of twin bore ophthalmologic tubing 40 can be made from materials having relatively low hardness. End portions 52 and 56 can therefore cause little or no reactions as surgical personnel navigate handpiece 14 about various surgical sites. Accordingly, end portions 52 and 56 can provide high navigability of handpiece 14. Other portions 54 of twin bore ophthalmologic tubing 40 can be made of materials having relatively high hardness thereby permitting no, or little, overall compliance of irrigation tube 46 and aspiration tube 48.

In some embodiments, end portions 52 and 56 can have a hardness of about 60 shore A to about 70 shore A while mid portion 54 can have a hardness of about 80 shore A to about 90 shore A. End portions 52 and 56 can be any length. However, in some embodiments, lengths 11 and 13 of end portions 52 and 56 can be about 6" to about 12" long. Mid portion 54 can be any length 12 although in some embodiments length 12 is about 6 feet.

Twin bore ophthalmologic tubing 40 can be made as a continuous extrusion in various embodiments. For instance, proximal end portion 52 can be extruded from one material (for instance a certain polymer). As the extrusion of proximal end portion 52 ends and the extrusion of mid portion 54 begins, a transition from the first material to a second material can occur within the feed system of the extruder. As the extrusion of mid portion 54 ends and the extrusion of distal end portion begins, a transition from the second material to a third material can occur. Thus, by using chemically and mechanically compatible materials before and after material transitions, twin bore ophthalmologic tubing 40 with portions 52, 54, and 56 of differing hardness can be created according to embodiments.

Different (or the same) materials can be fed to the extruder for irrigation tube 46 and for aspiration tube 48 during various phases of the extrusion of twin bore ophthalmologic tubing 40. Thus, twin bore ophthalmologic tubing 40 can be created in which corresponding portions of irrigation tube 46 and aspiration tube 48 have differing or about the same hardness. In some embodiments, portions 52, 54, and 56 can be formed by extruding a common material, but injecting various hardeners (or concentrations thereof) into the common material during differing phases of the extrusion. Portions 52, 54, and 56 of differing hardness can be created from a common material via post processing of such portions in some embodiments. For instance, twin bore ophthalmologic tubing 40 can be post-processed chemically to soften the "as formed" material to a select hardness for end portions 52 and 56.

In some embodiments, radiation can be used to harden overall twin bore ophthalmologic tubing 40 to a select hardness for end portions 52 and 56. Certain portions, such as mid portion 54, can be further exposed to radiation to further harden such portions 54 to another select, and higher, hardness. More particularly, in some embodiments, twin bore ophthalmologic tubing 40 can be coiled up and exposed to radiation to sterilize twin bore ophthalmologic tubing 40. In exposing twin bore ophthalmologic tubing 40 to radiation, mid portions 54 can be pre-positioned for radiation exposure, while end portions 52 and 56 can be pre-positioned to extend from coils of twin bore ophthalmologic tubing 40. By selectively applying radiation to mid portions 54, mid portions 54 can be exposed to radiation, sterilized, and hardened while end portions 52 and 56 remain relatively unexposed and relatively un-hardened. In some embodiments, all of twin bore ophthalmologic tubing 40 can be radiation sterilized with mid portions 54 being exposed to radiation for longer durations than end portions 52 and 56. In some embodiments, some (for instance, end portions 52 and 56) or all of twin bore ophthalmologic tubing 40 can be chemically sterilized (by, for instance, exposure to ethylene oxide (ETO) gas).

Embodiments provide twin bore ophthalmologic tubing with low compliance and low resistance to movement (even when connected to surgical handpieces and fluidics modules). Embodiments provide twin bore ophthalmologic tubing with rapid vacuum rise times in the aspiration line. Twin bore ophthalmologic tubing of embodiments are provided which allow compliance, navigability, and vacuum characteristics to be controlled by selecting hardness levels for various portions of the twin bore ophthalmologic tubing. Thus, twin bore ophthalmologic tubing of embodiments can increase the speed, efficiency, and accuracy of ophthalmologic procedures such as phacoemulsification, liquefaction, etc.

Although embodiments have been described in detail herein, it should be understood that the description is by way of example only and is not to be construed in a limiting sense. It is to be further understood, therefore, that numerous changes in the details of the embodiments and additional embodiments will be apparent, and may be made by, persons of ordinary skill in the art having reference to this description. It is contemplated that all such changes and additional embodiments are within scope of the claims below and their legal equivalents.

What is claimed is:

1. An ophthalmologic twin bore fluidics tubing for use with a fluidics module and a handpiece of an ophthalmologic system, the twin bore ophthalmologic tubing comprising:
   a first tube; and
   a second tube;
   wherein the first and second tubes have ends adapted for connection to the fluidics module and to the handpiece, the first and the second tubes being joined along substantially a length of the twin bore ophthalmologic tubing, the second tube having a first, second, and third portion with respective first, second, and third hardness, the first hardness being greater than the second hardness and the third hardness;
   wherein the first portion forms the mid portion than includes a majority of the length of the twin bore ophthalmologic tubing,
   wherein the second portion forms a first end portion on one side of the mid portion and the third portion forms a second end portion on an opposite side of the mid portion of the twin bore ophthalmologic tubing such that the first end portion is configured to attach to the handpiece and the second end portion is configured to attach to the console;
   wherein the first tube has a single hardness throughout the first tube.

2. The ophthalmologic twin bore fluidics tubing of claim 1, wherein the first tube hardness is less than the first hardness.

3. The ophthalmologic twin bore fluidics tubing of claim 1, wherein the first tube is an irrigation tube.

4. The ophthalmologic twin bore fluidics tubing of claim 1, wherein the second tube is an aspiration tube.

5. The ophthalmologic twin bore fluidics tubing of claim 1, wherein the first tube and the second tube are co-extruded.

\* \* \* \* \*